US007524061B2

United States Patent
Yan et al.

(10) Patent No.: US 7,524,061 B2
(45) Date of Patent: Apr. 28, 2009

(54) SYSTEM AND METHOD FOR ROBUST OPTIC DISK DETECTION IN RETINAL IMAGES USING VESSEL STRUCTURE AND RADON TRANSFORM

(75) Inventors: Michelle Xiao-Hong Yan, Princeton, NJ (US); Ke Huang, East Lansing, MI (US); Hans Schüll, Weisendorf (DE)

(73) Assignee: Siemens Corporate Research, Inc., Princeton, NJ (US)

( * ) Notice: Subject to any disclaimer, the term of this patent is extended or adjusted under 35 U.S.C. 154(b) by 270 days.

(21) Appl. No.: 11/539,691

(22) Filed: Oct. 9, 2006

(65) Prior Publication Data

US 2007/0109499 A1    May 17, 2007

Related U.S. Application Data

(60) Provisional application No. 60/726,047, filed on Oct. 12, 2005.

(51) Int. Cl.
  *A61B 3/14* (2006.01)
(52) U.S. Cl. ...................................... 351/206
(58) Field of Classification Search ............. 351/206
  See application file for complete search history.

(56) References Cited

U.S. PATENT DOCUMENTS 5,311,600 A * 5/1994 Aghajan et al. ............. 382/156

2006/0147095 A1 * 7/2006 Usher et al. ................. 382/117

OTHER PUBLICATIONS

E. Corona, S. Mitra, M. Wilson, T. Krile, Y. Kwon and P. Soliz, "Digital stereo image analyzer for generating automated 3-d measures of optic disc deformation in glaucoma", IEEE Transactions on Medical Imaging, vol. 21, No. 10, pp. 1244-1253, 2002.
H. Li, W. Hsu, M. Lee and T. Wong, "Automatic grading of retinal vessel caliber", IEEE Transactions on Biomedical Engineering, vol. 52, No. 7, pp. 1352-1355, 2005.
H. Li and O. Chutatape, "A model-based approach for automated feature extraction in fundus images", Proceedings of 9th IEEE International Conference on Computer Vision (ICCV), 2003.
E. Trucco and P. Kamat, "Locating the optic disk in retinal images via plausible detection and constraint satisfaction", Proceedings of 2004 International Conference on Image Processing (ICIP04), 2004.
M. Lalonde, M. Beaulieu, and L. Gagnon, "Fast and robust optic disc detection using pyramidal decomposition and hausdorff-based template matching", IEEE Transactions on Medical Imaging, vol. 20, No. 11, pp. 1193-1200, 2001.

(Continued)

*Primary Examiner*—Jessica T Stultz
*Assistant Examiner*—Mahidere S Sahle

(57) ABSTRACT

A method for optic disk detection in retinal images, includes: extracting a vessel tree from a retinal image; locating an optic disk in the retinal image using the vessel tree; enhancing a contrast of the optic disk; removing vessels from the contrast enhanced optic disk; detecting a boundary of the optic disk with vessels removed by generating an edge map; projecting the edge map at a plurality of angles by using a radon transform; and estimating a radius and center of the optic disk using the projections.

20 Claims, 12 Drawing Sheets

OTHER PUBLICATIONS

R. Abdel-Ghafar, T. Morris, T. Ritchings and I. Wood, "Detetion and characterisation of the optic disk in glaucoma and diabetic retinopathy", Proceedings of Medical Image Understand and Analysis, 2004.

A. Osareh, M. Mirmehdi, B. Thomas and R. Markham, "Colour morphology and snakes for optic disk localization", Proceedings of Medical Image Understanding and Analysis, 2001.

A. Hoover and M. H. Goldbuam, "Locating the optic nerve in a retinal image using the fuzzy convergence of the blood vessels", IEEE Transactions on Medical Imaging, vol. 22, No. 8, pp. 951-958, 2003.

M. Foracchia, E. Grisan and A. Ruggeri, "Detection of optic disc in retinal images by means of a geometrical model of vessel structure", IEEE Transactions on Medical Imaging, vol. 23, No. 10, pp. 1189-1195, 2004.

C. Kirbas and F. Quek, "A review of vessel extraction techniques and algorithms", ACM Computing Survey, vol. 36, No. 2, pp. 81-121, 2004.

K. Huang and M. Yan, "A local adaptive algorithm for microaneurysms detection in digital fundus images", Proceedings of Computer Vision for Biomedical Image Applications: Current Techniques and Future Trends, International Conference on Computer Vision Workshop, 2005.

N. Otsu, "A threshold selection method from gray-level histograms", IEEE Transactions on Systems, Man, and Cybernetics, vol. 9, No. 1, pp. 62-66, 1979.

* cited by examiner

SYSTEM AND METHOD FOR ROBUST OPTIC DISK DETECTION IN RETINAL IMAGES USING VESSEL STRUCTURE AND RADON TRANSFORM

CROSS-REFERENCE TO RELATED APPLICATION

This application claims the benefit of U.S. Provisional Application No. 60/726,047, filed Oct. 12, 2005, a copy of which is herein incorporated by reference.

BACKGROUND OF THE INVENTION

1. Technical Field

The present invention relates to optic disk detection in retinal images, and more particularly, to a system and method for robust optic disk detection in retinal images using vessel structure and radon transform.

2. Discussion of the Related Art

Structural analysis of retinal images is critical to screening and diagnosis of eye diseases such as glaucoma, diabetic retinopathy and age-related macular degeneration. Estimating the location and size of an optic disk is needed in clinical applications such as measuring the progression of glaucoma as described in L. Bonomi and N. Orzalesi, Glaucoma: Concepts in Evolution: Morphometric and Functional Parameters in the Diagnosis and Management of Glaucoma. Kugler Ghendini, 1991, and E. Corona, S. Mitra, M. Wilson, T. Krile, Y. Kwon and P. Soliz, "Digital stereo image analyzer for generating automated 3-d measures of optic disc deformation in glaucoma", IEEE Transactions on Medical Imaging, vol. 21, no. 10, pp. 1244-1253, 2002; providing a reference point to a macular that is the critical region for diabetic retinopathy diagnosis as described in T. Dorion, Manual of Ocular Fundus Examination. Butterworth-Heinemann, 1998; and identifying a concentric area where an arteriolar-to-venular diameter ratio (AVR) is measured for cardiovascular disease diagnosis as described in L. Hubbard, R. Brothers and et al., "Methods for evaluation of retinal microvascular abnormalities associated with hypertension/sclerosis in the atherosclerosis risk in communities study", Ophthalmology, vol. 106, no. 12, pp. 2269-2280, 1999, and H. Li, W. Hsu, M. Lee and T. Wong, "Automatic grading of retinal vessel caliber", IEEE Transactions on Biomedical Engineering, vol. 52, no. 7, pp. 1352-1355, 2005. Detection of an optic disk usually includes two steps: the first is the localization of a candidate region or nerve head, which should be inside an optic disk and the second is the detection of a boundary of the optic disk.

In a retinal image, the optic disk appears to be a round-disk like region with high intensity values. Physiologically, an optic disk is where the vessels, including arteries and veins, emerge and branch out to form a tree structure. An illustration of an optic disk is given in FIG. 1. Optic disks appear to be the brightest part in most retinal images. This property has often been used to located possible candidate regions by clustering pixels with highest brightness values as described in H. Li and O. Chutatape, "A model-based approach for automated feature extraction in fundus images", Proceedings of 9$^{th}$ IEEE International Conference on Computer Vision (ICCV), 2003, M. L. P. Pallawala, W. Hsu and K. G. Eone, "Automated optic disc localization and contour detection using ellipse fitting and wavelet transform", Proceedings of 8$^{th}$ European Conference on Computer Vision (ECCV), 2004, E. Trucco and P. Kamat, "Locating the optic disk in retinal images via plausible detection and constraint satisfaction", Proceedings of 2004 International Conference on Image Processing (ICIP04), 2004, and M. Lalonde, M. Beaulieu, and L. Gagnon, "Fast and robust optic disc detection using pyramidal decomposition and hausdorff-based template matching", IEEE Transactions on Medical Imaging, vol. 20, no. 11, pp. 1193-1200, 200 1, or by using a matched filter or Hough transform to detect a round region as described in H. Li, W. Hsu, M. Lee and T. Wong, "Automatic grading of retinal vessel caliber", IEEE Transactions on Biomedical Engineering, vol. 52, no. 7, pp. 1352-1355, 2005, R. Abdel-Ghafar, T. Morris, T. Ritchings and I. Wood, "Detection and characterisation of the optic disk in glaucoma and diabetic retinopathy", Proceedings of Medical Image Understanding and Analysis, 2004, and A. Osareh, M. Mirmehdi, B. Thomas and R. Markham, "Colour morphology and snakes for optic disk localization", Proceedings of Medical Image Understanding and Analysis, 2001. However, the assumption that an optic disk is the brightest area in a retinal image does not always hold. Counter examples are given in A. Hoover and M. H. Goldbuam, "Locating the optic nerve in a retinal image using the fuzzy convergence of the blood vessels", IEEE Transactions on Medical Imaging, vol. 22, no. 8, pp. 951-958, 2003, where lesions or hemorrhages in unhealthy eyes may obscure optic disks and generate bright round structures elsewhere. Even with healthy eyes, uneven illumination may cause some regions to be brighter, thus invalidating the assumption.

Compared with brightness-based methods, using vessel structure is more robust and stable for optic disk localization, since neither eye diseases nor uneven illumination changes the fact that the root of a vessel tree is always inside an optic disk. In A. Hoover and M. H. Goldbuam, "Locating the optic nerve in a retinal image using the fuzzy convergence of the blood vessels", IEEE Transactions on Medical Imaging, vol. 22, no. 8, pp. 951-958, 2003, the root of a vessel tree is assumed to have the highest vessel density and optic disks are detected by fuzzy convergence. A parabola is imposed on a retinal image as described in M. Foracchia, E. Grisan and A. Ruggeri, "Detection of optic disc in retinal images by means of a geometrical model of vessel structure", IEEE Transactions on Medical Imaging, vol. 23, no. 10, pp. 1189-1195, 2004, to segment the vessels into four parts. The parameters of a parabola are obtained by maximizing the difference between the vessel directions inside and outside the parabola. The vertex of an optimized parabola is defined as the location of an optic disk. The vessel-based detection as described in C. Kirbas and F. Quek, "A review of vessel extraction techniques and algorithms", ACM Computing Survey, vol. 36, no. 2, pp. 81-121, 2004, is computationally intensive due to the requirement for accurate vessel detection as pointed out in H. Li and O. Chutatape, "A model-based approach for automated feature extraction in fundus images", Proceedings of 9$^{th}$ IEEE International Conference on Computer Vision (ICCV), 2003. The assumption underlying the method described in A. Hoover and M. H. Goldbuam, "Locating the optic nerve in a retinal image using the fuzzy convergence of the blood vessels", IEEE Transactions on Medical Imaging, vol. 22, no. 8, pp. 951-958, 2003 may not always be true. For example, in retinal images with tortuosity, a non-optic disk area may have higher vessel density than inside the optic disk. As for the method in M. Foracchia, E. Grisan and A. Ruggeri, "Detection of optic disc in retinal images by means of a geometrical model of vessel structure", IEEE Transactions on Medical Imaging, vol. 23, no. 10., pp. 1189-1195, 2004, parameters to be optimized in the objective function are chosen to be proportional to vessel caliber, and simulated annealing is adopted to optimize the objective function.

SUMMARY OF THE INVENTION

In an exemplary embodiment of the present invention, a method for optic disk detection in retinal images, comprises: extracting a vessel tree from a retinal image; locating an optic disk in the retinal image using the vessel tree; enhancing a contrast of the optic disk, removing vessels from the contrast enhanced optic disk; detecting a boundary of the optic disk with vessels removed by generating an edge map; projecting the edge map at a plurality of angles by using a radon transform; and estimating a radius and center of the optic disk using the projections.

Extracting a vessel tree from a retinal image comprises: applying shade correction and contrast enhancement to the retinal image; and performing a binarization on the shade corrected and contrast enhanced retinal image. Locating an optic disk in the retinal image comprises: selecting first start and end points and second start and end points from different branches of the vessel tree; finding a shortest path between the first start and end points and a shortest path between the second start and end points; finding an intersecting point of the shortest paths at a root of the vessel tree; and defining the intersecting point as a location of the optical disk.

Selecting first start and end points and second start and end points from different branches of the vessel tree comprises: defining a top-left point in the vessel tree as the first start point; defining a bottom-right point in the vessel tree as the first end point; defining a top-right point in the vessel tree as the second start point; and defining a bottom-left point in the vessel tree as the second end point.

The shortest paths are found by using a searching algorithm. The method further comprises cropping the optic disk before enhancing a contrast of the optic disk. Removing vessels from the contrast enhanced optic disk comprises applying a morphological filter to the cropped optic disk. Generating the edge map comprises applying an edge detection filter to the cropped optic disk. The method further comprises applying a threshold to the edge map to obtain a binary map.

The method further comprises: before estimating a radius and center of the optic disk using the projections, identifying a portion of an edge map projected at one of the angles as the boundary of the optic disk; and trimming left and right sides of the boundary of the optic disk.

The method further comprises: when estimating a radius and center of the optic disk using the projections, computing a mean and standard deviation of each of three sequences, each sequence including an estimated value of a center or radius of the optic disk using the Radon transforms projected at each of the angles; removing values from each of the sequences that are not within two standard deviations from each sequence's mean; and estimating the radius and center of the optic disk by taking the mean of the remaining values of these sequences.

In an exemplary embodiment of the present invention, a system for optic disk detection in retinal images, comprises: a memory device for storing a program; a processor in communication with the memory device, the processor operative with the program to: extract a vessel tree from a retinal image; locate an optic disk in the retinal image using the vessel tree; enhance a contrast of the optic disk; remove vessels from the contrast enhanced optic disk; detect a boundary of the optic disk with vessels removed by generating an edge map; project the edge map at a plurality of angles by using a radon transform; and estimate a radius and center of the optic disk using the projections.

When extracting a vessel tree from a retinal image the processor is further operative with the program to: apply shade correction and contrast enhancement to the retinal image; and perform a binarization on the shade corrected and contrast enhanced retinal image. When locating an optic disk in the retinal image the processor is further operative with the program to: select first start and end points and second start and end points from different branches of the vessel tree; find a shortest path between the first start and end points and a shortest path between the second start and end points; find an intersecting point of the shortest paths at a root of the vessel tree; and define the intersecting point as a location of the optical disk.

When selecting first start and end points and second start and end points from different branches of the vessel tree the processor is further operative with the program to: define a top-left point in the vessel tree as the first start point; define a bottom-right point in the vessel tree as the first end point; define a top-right point in the vessel tree as the second start point; and define a bottom-left point in the vessel tree as the second end point.

The shortest paths are found by using a searching algorithm. The processor is further operative with the program to crop the optic disk before enhancing a contrast of the optic disk. When removing vessels from the contrast enhanced optic disk the processor is further operative with the program to: apply a morphological filter to the cropped optic disk. When generating the edge map the processor is further operative with the program to apply an edge detection filter to the cropped optic disk. The processor is further operative with the program to apply a threshold to the edge map to obtain a binary map.

Before estimating a radius and center of the optic disk using the projections the processor is further operative with the program to: identify a portion of an edge map projected at one of the angles as the boundary of the optic disk; and trim left and right sides of the boundary of the optic disk.

When estimating a radius and center of the optic disk using the projections the processor is further operative with the program to: compute a mean and standard deviation of each of three sequences, each sequence including an estimated value of a center or radius of the optic disk using the Radon transforms projected at each of the angles; remove values from each of the sequences that are not within two standard deviations from each sequences mean; and estimate the radius and center of the optic disk by taking the mean of the remaining values of these sequences.

In an exemplary embodiment of the present invention, a computer program product comprises a computer useable medium having computer program logic recorded thereon for optic disk detection in retinal images, the computer program logic comprising: program code for extracting a vessel tree from a retinal image; program code for locating an optic disk in the retinal image using the vessel tree; program code for enhancing a contrast of the optic disk; program code for removing vessels from the contrast enhanced optic disk; program code for detecting a boundary of the optic disk with vessels removed by generating an edge map; program code for projecting the edge map at a plurality of angles by using a radon transform; and program code for estimating a radius and center of the optic disk using the projections.

In an exemplary embodiment of the present invention, a system for optic disk detection in retinal images, comprises: a fundus camera for acquiring a retinal image; and an optic disk detection module for extracting a vessel tree from the retinal image; locating an optic disk in the retinal image using the vessel tree; enhancing a contrast of the optic disk; removing vessels from the contrast enhanced optic disk; detecting a boundary of the optic disk with vessels removed by generating an edge map; projecting the edge map at a plurality of angles by using a radon transform; and estimating a radius and center of the optic disk using the projections.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Figure 2:
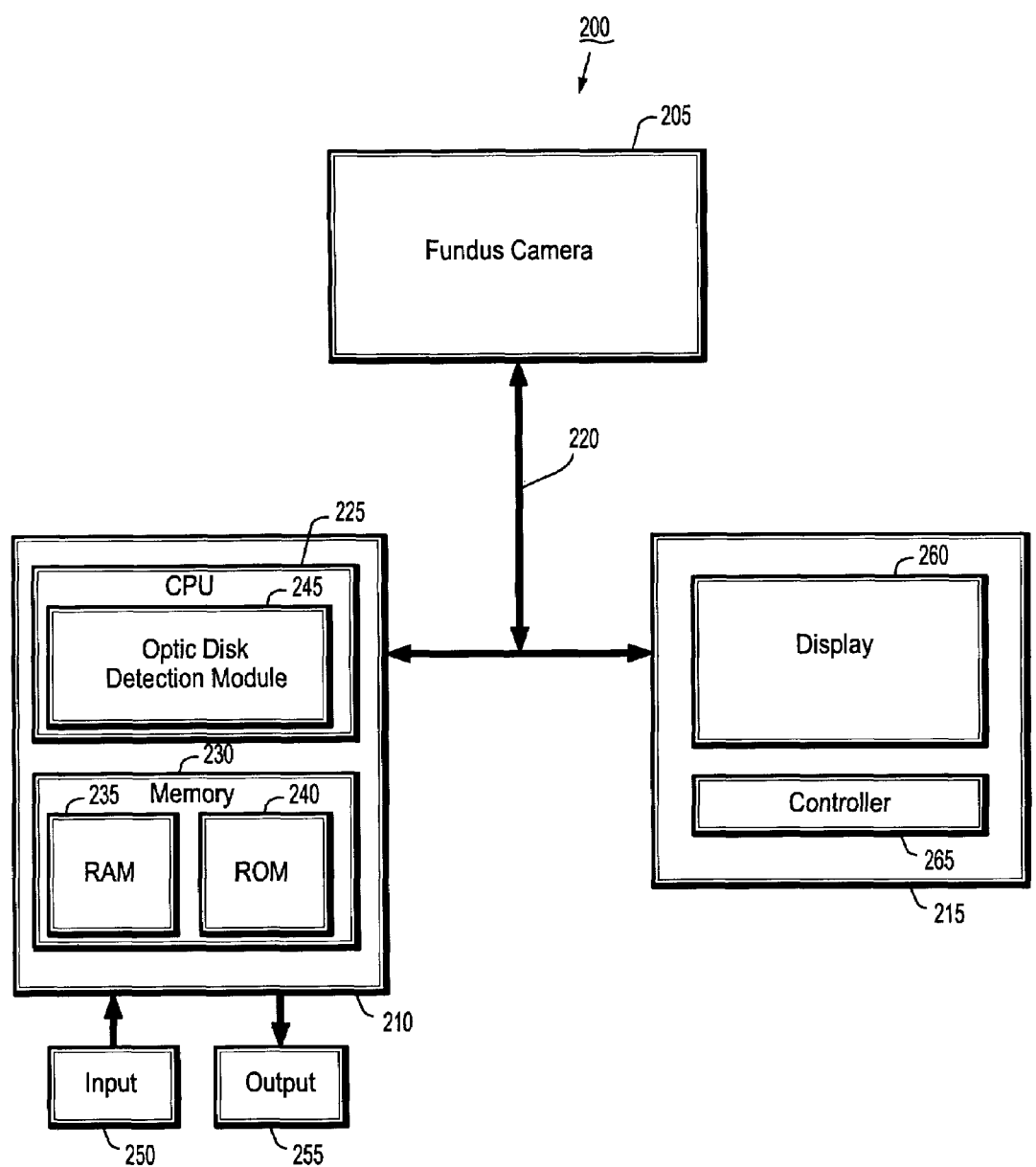
FIG. 2 illustrates a system for robust optic disk detection in retinal images using vessel structure and radon transform according to an exemplary embodiment of the present invention.

FIG. 2 illustrates a system 200 for robust optic disk detection in retinal images using vessel structure and radon transform according to an exemplary embodiment of the present invention. As shown in FIG. 2, the system 200 includes a fundus camera 205, a PC 210 and an operator's console 215 connected over a wired or wireless network 120.

The fundus camera 205 is a device used by optometrists, ophthalmologists, and other trained medical professional to photograph a patient's retina. The fundus camera 205 is generally used for monitoring progression of a disease, diagnosis of a disease (combined with retinal angiography), or in screening programs, where the photos can be analyzed later.

The PC 210, which may be a portable or laptop computer, includes a CPU 225 and a memory 230 connected to an input device 250 and an output device 255. The CPU 225 includes an optic disk detection module 245 that includes one or more methods for robust optic disk detection in retinal images using vessel structure and radon transform to be discussed hereinafter with reference to FIGS. 3-12. Although shown inside the CPU 225, the optic disk detection module 245 can be located outside the CPU 225. Further, the system 200 can also be a stand-alone unit embodying the fundus camera 205, PC 210 and/or operator's console 215.

The memory 230 includes a RAM 235 and a ROM 240. The memory 230 can also include a database, disk drive, tape drive, etc., or a combination thereof. The RAM 235 functions as a data memory that stores data used during execution of a program in the CPU 225 and is used as a work area. The ROM 240 functions as a program memory for storing a program executed in the CPU 225. The input 250 is constituted by a keyboard, mouse, etc., and the output 255 is constituted by an LCD, CRT display, printer, etc.

The operation of the system 200 can be controlled from the operator's console 215, which includes a controller 265, e.g., a keyboard, and a display 260. The operator's console 215 communicates with the PC 110 and the fundus camera 205 so that image data collected by the fundus camera 205 can be rendered by the PC 210 and viewed on the display 260. The PC 210 can be configured to operate and display information provided by the fundus camera 205 absent the operator's console 215, by using, e.g., the input 250 and output 255 devices to execute certain tasks performed by the controller 265 and display 260.

The operator's console 215 may further include any suitable image rendering system/tool/application that can process digital image data of the fundus camera 205 to generate and display images on the display 260. More specifically, the image rendering system may be an application that provides rendering and visualization of fundus image data, and which executes on a general purpose or specific computer workstation. The PC 210 can also include the above-mentioned image rendering system/tool/application.

As mentioned in the Background section of this disclosure, vessels coming from a brain emerge at an optic disk and branch out to form a tree structure in a retinal image. Thus, the root of a vessel tree is inside an optic disk. The steps involved in optic disk detection to be discussed below are based on graph theory supported by physiological evidence. It is proven in graph theory that there is only one path between any two nodes in any given tree structure, and the root node is in the path if the two nodes are not in the same branch. Taking this into account, a method for localizing an optic disk from a retinal image I according to an exemplary embodiment of the present invention will now be described with reference to FIG. 3.

Figure 3:
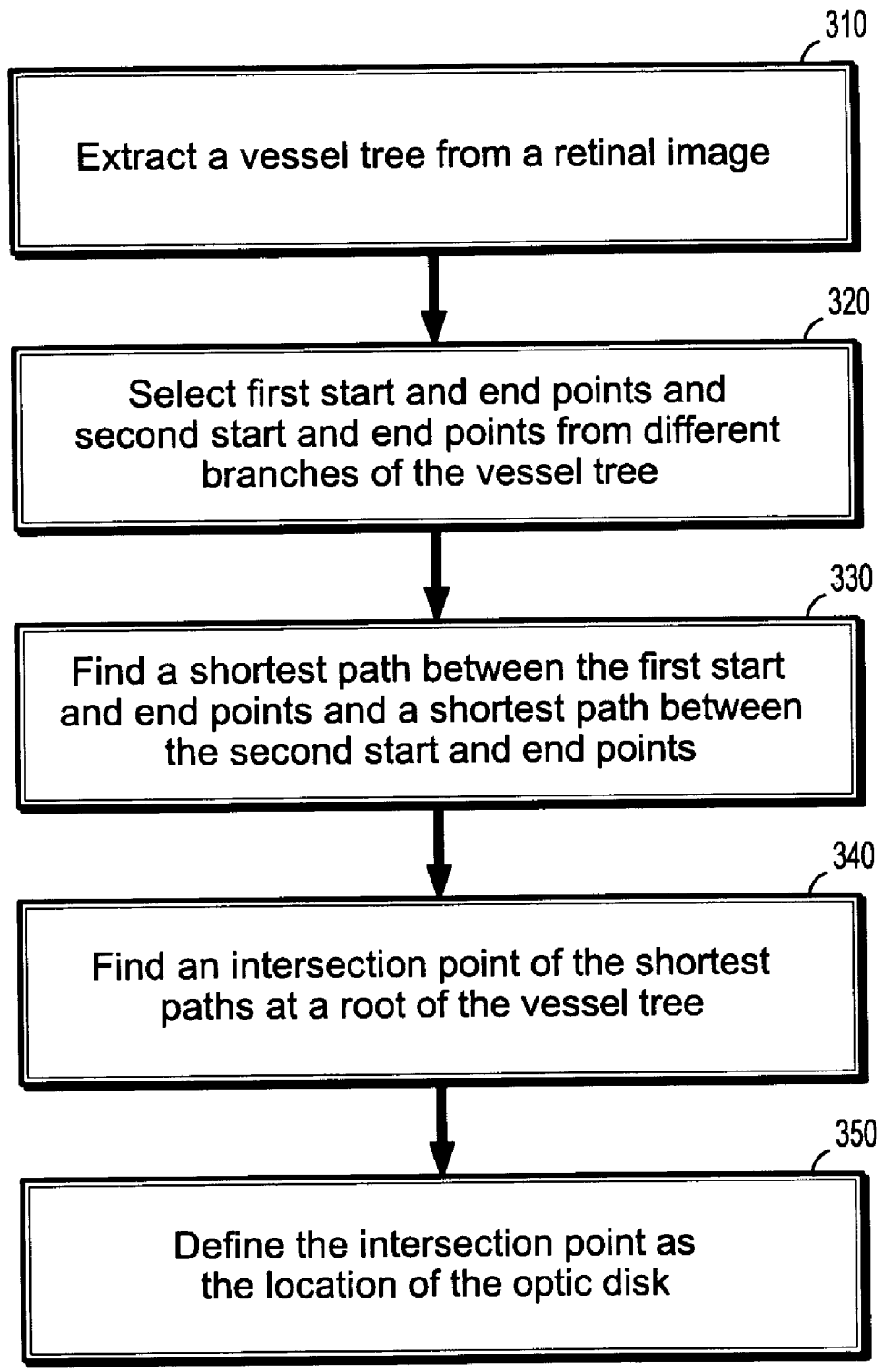
FIG. 3 illustrates a method for optic disk localization with vessel structure according to an exemplary embodiment of the present invention.

As shown in FIG. 3, a vessel tree VT is extracted from the retinal image I (310). Here, VT is a binary image, and VT(i, j)=1 indicates that the pixel I(i,j) is on a vessel branch; otherwise, the pixel I(i,j) corresponds to a non-vessel location. Two start points $S_1$, $S_2$ and two end points $E_1$, $E_2$ are selected from the vessel tree VT (320). In this step, $S_1$, $S_2$ and $E_1$, $E_2$ are selected from different branches of the vessel tree VT. A shortest path $P_1$ between $S_1$ and $E_1$ and a shortest path $P_2$ between $S_2$ and $E_2$ are found (330). An intersection point L of $P_1$ and $P_2$ is found at a root of the vessel tree VT=$P_1 \cap P_2$ (340). The intersection point L is defined as the location of the optic disk (350).

A detailed description of the steps outlined in FIG. 3 beginning first with vessel stricture extraction followed by optic disk localization will now be presented.

Traditional vessel extraction techniques as described in Kirbas and F. Quek, "A review of vessel extraction techniques and algorithms", ACM Computing Survey, vol. 36, no. 2, pp. 81-121, 2004, can be time consuming and thus have become a major obstacle for using the information from a vessel structure for optic disk detection. However, the method outlined in FIG. 3 does not require accurate detection of a vessel structure. It only requires tat the entire detected vessel tree be connected such that the path between any two nodes on the tree can be found where the detected vessel does not have to be complete, or to have the exact caliber of the actual vessel. The root of a detected vessel serves as the location of an optic disk. A two-level binarization algorithm developed for vessel tree detection based on these requirements is now discussed.

Structures in retinal images containing blood are best contrasted in a green channel, thus green channel images are used for vessel detection. Binarization of an original green channel image does not generate a reasonable result due to uneven illumination and other varying image conditions. To tackle this, shade correction and contrast enhancement as described in K. Huang and M. Yan, "A local adaptive algorithm for microaneurysms detection in digital fundus images", Proceedings of Computer Vision for Biomedical Image Applications: Current Techniques and Future Trends, International Conference on Computer Vision Workshop, 2005, a copy of which is incorporated by reference herein in its entirety, is applied to enhance an image before binarization. The purpose of shade correction is to correct background variations and reduce the effect introduced by different physiological properties of the retina and non-uniform illumination across the field of view.

Figure 4:
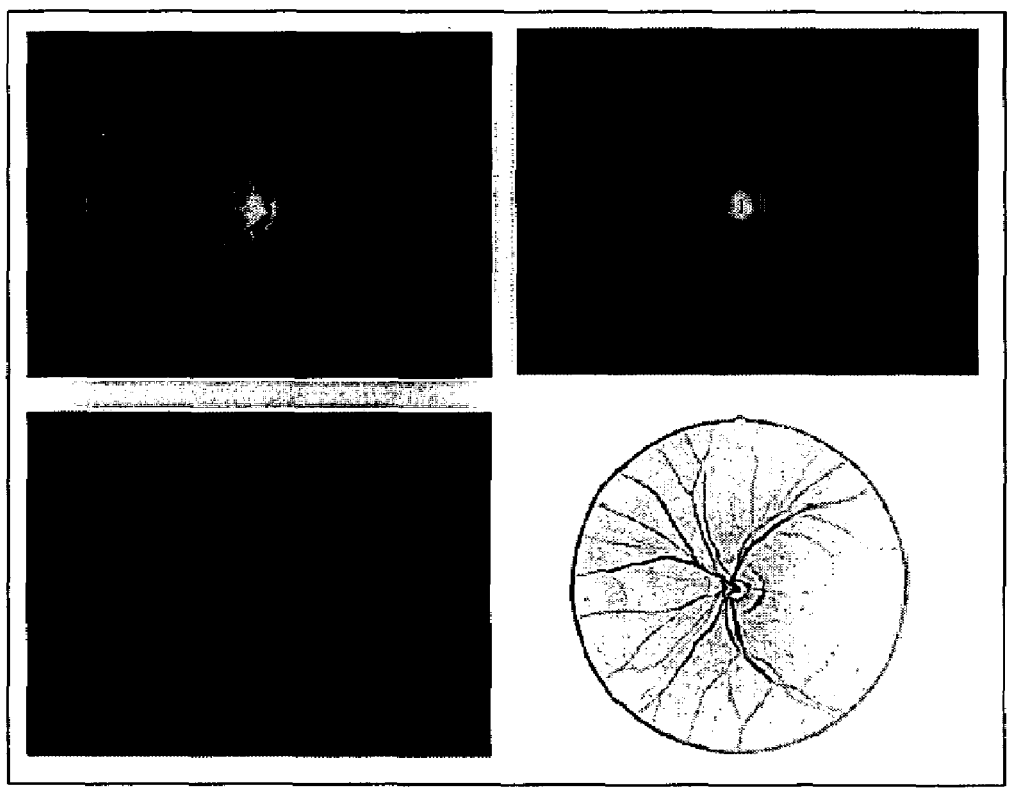
FIG. 4 illustrates effects of shade correction and contrast enhancement on a retinal image when using a binarization algorithm according to an exemplary embodiment of the present invention.

Effects of shade correction and contrast enhancement are illustrated in FIG. 4, where the top-left image is a green channel image, top-right image is an estimated background image, bottom-left image is a difference image between the green channel image and background image and the bottom-right image is the difference image after contrast enhancement and smoothing. FIG. 4 clearly shows that major vessels are enhanced across the entire image.

Figure 1:
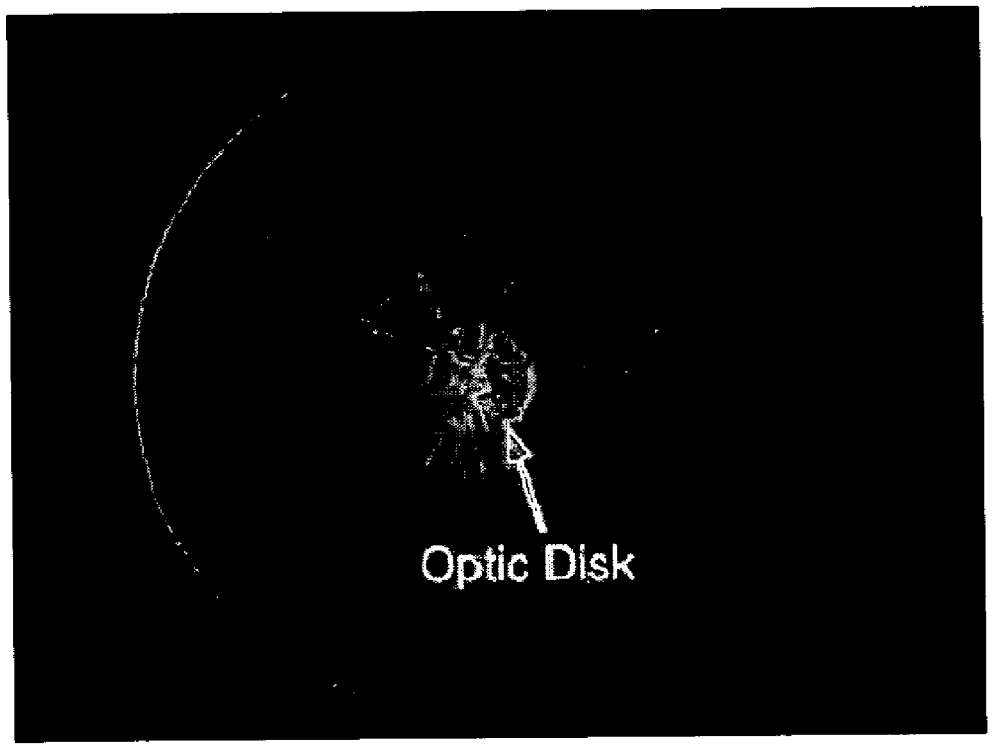
FIG. 1 illustrates an optic disk in a retinal image.
Figure 5:
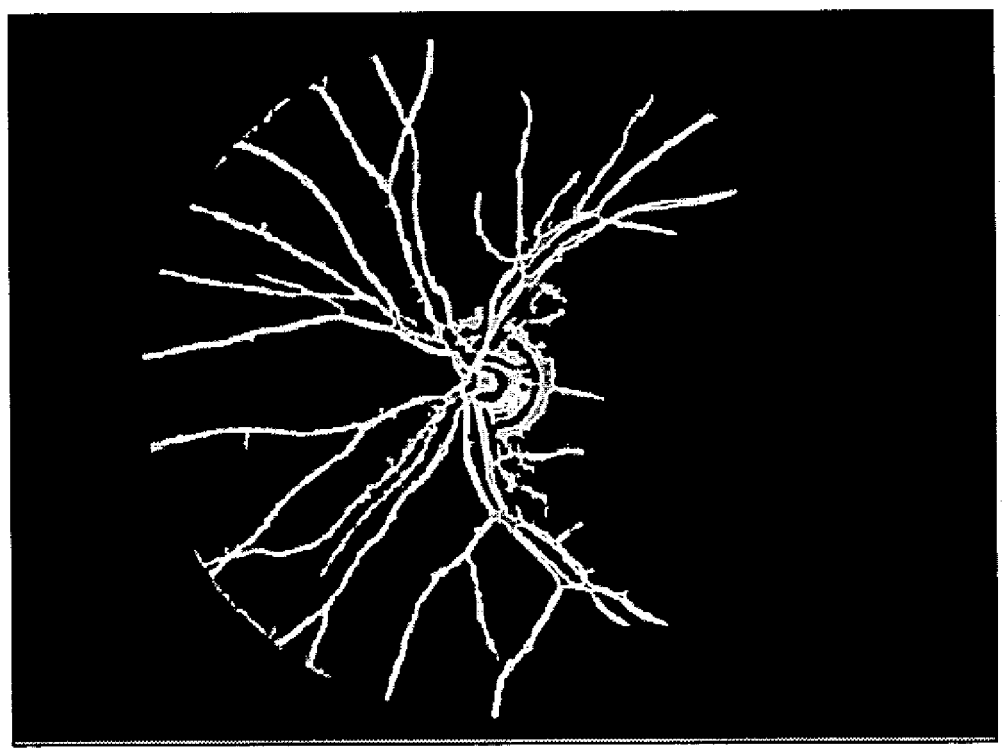
FIG. 5 illustrates a vessel tree detected using the binarization algorithm according to an exemplary embodiment of the present invention.

Binarization is then performed on an enhanced difference image with a threshold that is estimated from its histogram using the algorithm introduced in N. Otsu, "A threshold selection method from gray-level histograms", IEEE Transactions on Systems, Man, and Cybernetics, vol. 9, no. 1, pp. 62-66, 1979, a copy of which is incorporated by reference herein in its entirety. Not all vessel structures can be detected in this step for many reasons since, for example, vessels may be located at different depths or have non-uniform illumination. Vessels close to a retina surface are often easier to detect than ones that are far from the surface. To detect fine vessels (e.g., vessels that are far from the surface), another binarization step is introduced. Here, the vessel structures currently detected are removed and the rest of the image is processed again following the same steps: shade correction, contrast enhancement and binarization. As a result, the vessels detected from these two steps are combined to form a connected component with a largest size, which is defined as the vessel tree VT. A vessel tree detected from the image in FIG. 1 is illustrated in FIG. 5. It is noted that in the detected vessel tree, a circle like artifact is generated at a boundary during shade correction and contrast enhancement, which can be easily removed using an original foreground template.

As shown in FIG. 5, some fine vessels are missing in the tree, and some artifacts are visible around the boundary of an optic disk and along the boundary of detected vessels. However, the method of FIG. 3 relies on major vessels that are normally among the easiest to detect near the region of an optic disk, thus missing vessels and artifacts do not cause the detection to fail. In addition, the missing vessels and artifacts do not obscure the fact that the obtained structure is a tree and that its root is inside an optic disk. Therefore, with the simple and efficient two-level binarization algorithm, the obtained vessel tree is considered to be sufficient for optic disk detection.

As previously mentioned, the points $S_1$, $S_2$ and $E_1$, $E_2$ should be selected from different branches of a vessel tree VT to make sure the intersection of paths $P_1$ and $P_2$ is the tree root. Prior knowledge is used here to help with the selection of $S_1$, $S_2$ and $E_1$, $E_2$. In order for eyes to see better, there should be no vessels in the macular region. Thus, no points should be placed in the macular region. In addition, the four points should be placed as far away from each other as possible so that the area formed by the points covers most of a retinal image. With a pixel location denoted as (i,j), and VT(i,j) is defined to be equal to 1 when (i,j) is on a tree, the points $S_1$, $S_2$ and $E_1$, $E_2$ are chosen as follows:

1) S1: the most top-left point.

$$(i, j) = \min_{k,l}(k + l), \quad s.t. \ VT(k, l) = 1$$

2) E1: the most bottom-right point.

$$(i, j) = \max_{k,l}(k + l), \quad s.t. \ VT(k, l) = 1$$

3) S2: the most top-right point.

$$(i, j) = \min_{k,l}(k - l), \quad s.t. \ VT(k, l) = 1$$

4) E2: the most bottom-left point.

$$(i, j) = \max_{k,l}(k - l), \quad s.t. \ VT(k, l) = 1$$

In this manner, $S_1$, $S_2$ and $E_1$, $E_2$ are selected such that it is guaranteed that they are as far from each other as possible. Thus, it is more likely that they are chosen from different branches of the vessel tree VT, and an optic disk is contained in the region formed by the four points.

Because a detected vessel branch may not be one pixel in width, searching its path is not as easy as compared to searching in a pure tree structure; however, the path can be solved by using a centerline. A search algorithm as described in S. Russell and P. Norvig, Artificial Intelligence: A Modem Approach (Second Edition). Prentice Hall, 2002, a copy of which is incorporated by reference herein in its entirety, can be used to search paths from detected vessels due to the complexity of the centerline detection. There are often multiple paths between two points selected from two different vessel branches due to the intersections among vessel branches and the artifacts introduced by the simple vessel detection algorithm. Therefore, the entire vessel structure is an approximation to a tree structure. It will now be discussed how the point selection process combined with the search for shortest paths can overcome approximation or mismatching.

Let $P_1$ denote the shortest path between $S_1$ and $E_1$, and $P_2$ denote the shortest path between $S_2$ and $E_2$. First, vessels at different depths in a 3D space are projected to a 2D retinal image during imaging, thereby generating some vessel intersections as shown, for example, in FIG. 5. However, these vessel intersections are not usually close to the region of an optical disk. Because of the shortest path constraint, these intersections should not have much impact on the searched paths $P_1$ and $P_2$. Second, considerable artifacts are generated along the boundary of an optic disk. Again, the shortest path constraint limits the interference to the searched paths. Take the path $P_1$ as an example, where $P_1$ is the shortest path between the most top-left point $S_1$ and the most bottom-right point $E_1$. Given the constraint of searching for the shortest path, $P_1$ is forced to cross an optic disk through vessel branches from its top-left corner to the bottom-right corner, rather than detouring trough the artifacts along the optic disk boundary.

The search algorithm defined in S. Russell and P. Norvig, Artificial Intelligence: A Modem Approach (Second Edition). Prentice Hall, 2002, is used to search for the shortest path between any two given points on a tree VT. Three functions are defined in the search algorithm: 1) a cost function g(n), which measures the cost from the start point to a point n; 2) a heuristic function h(n), which is an estimated cost from a point n to the end point; and 3) $f(n)=g(n)+h(n)$, which is an estimated cost from the start point to the end point. The search algorithm is guaranteed to find the shortest path if h(n) is admissible, i.e., the estimated cost h(n) is always less than the actual cost for reaching the end point from a point n. Given a vessel structure VT and each given pixel, the immediate neighboring eight pixels are searched for the shortest path. In S. Russell and P. Norvig, Artificial Intelligence: A Modem Approach (Second Edition). Prentice Hall, 2002, g(n) is defined as the number of pixels on the path from the start point to a point n. A natural definition for h(n) is the Euclidean distance measured in the unit of a pixel from a point n to the end point. Clearly, this heuristic function is admissible since it is the least possible cost from a point n to the end point. The search algorithm also maintains two lists; an open list that contains the points to be searched and a closed list that contains the searched points. With these definitions, the search algorithm is run as follows:

1) Initialize the open list to contain only the start point.
2) Initialize the closed list to empty.
3) Find the point with the least value of f(n) in the open list and denote it as C.
4) Remove C from the open list.
5) Put C in the closed list.
6) For each immediate neighbor of C, denote it as Q and do the following:
    (a) if Q is the end point, stop;
    (b) g(Q)=g(C)+1;
    (c) h(Q)=Euclidean distance from the end point;
    (d) f(Q)=g(Q)+h(Q);
    (e) if a node n in the open list has the same position and a lower g(n) value, discard Q;
    (f) if a node n in the closed list has the same position and a lower g(n) value, discard Q;
    (g) if Q is not discarded, put it in the open list;
7) Go to step 3.

Figure 6:
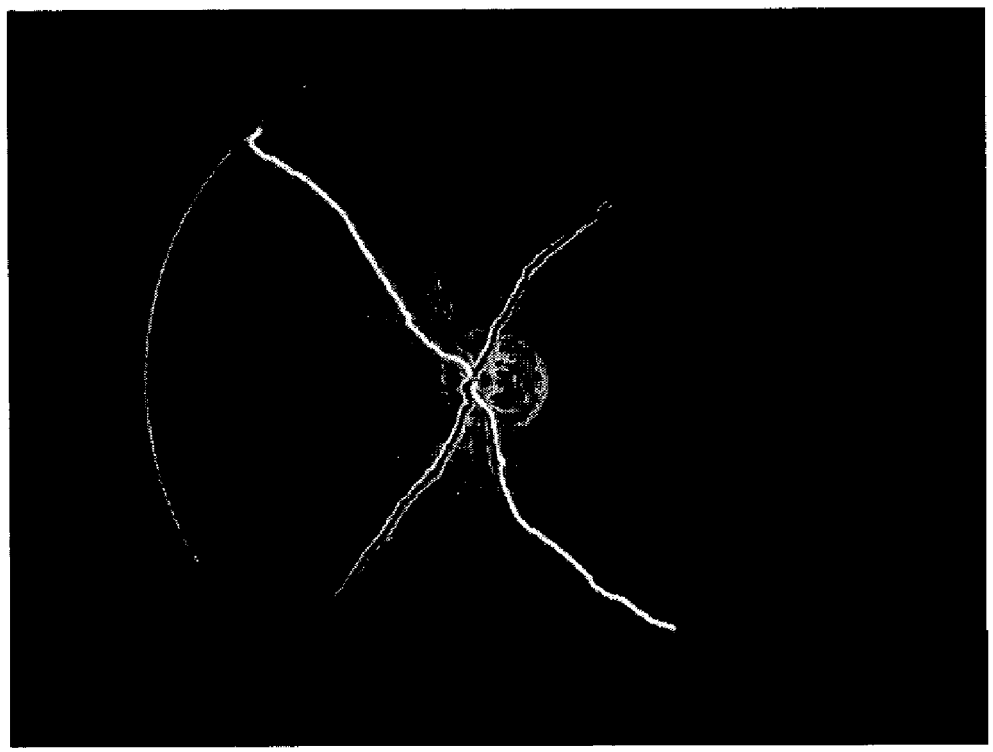
FIG. 6 illustrates optic disk detection using path intersection according to an exemplary embodiment of the present invention.

An example of point selection, path searching and intersection is illustrated in FIG. 6. As shown in FIG. 6, the two searched paths are one pixel wide; however, they are dilated to enhance their visibility. As can be seen, the two paths intersect at the root of a vessel tree structure.

An optic disk is a bright region that often has the best contrast in the blue channel of the color space. Therefore, the blue-channel retinal image is used for optic disk parameter estimation. Since the position of an optic disk has already been detected, a small region around the position is cropped and used for optic disk parameter estimation. For a retinal image of, for example, 1600×1200 pixels, a diameter of a normal optic disk is about 100 pixels. To avoid missing any part of the disk, a 400×400 pixel square C1 is cropped with the detected position at the center. Steps involved for optical disk parameter estimation according to an exemplary embodiment of the present invention are shown in FIG. 7.

Figure 7:
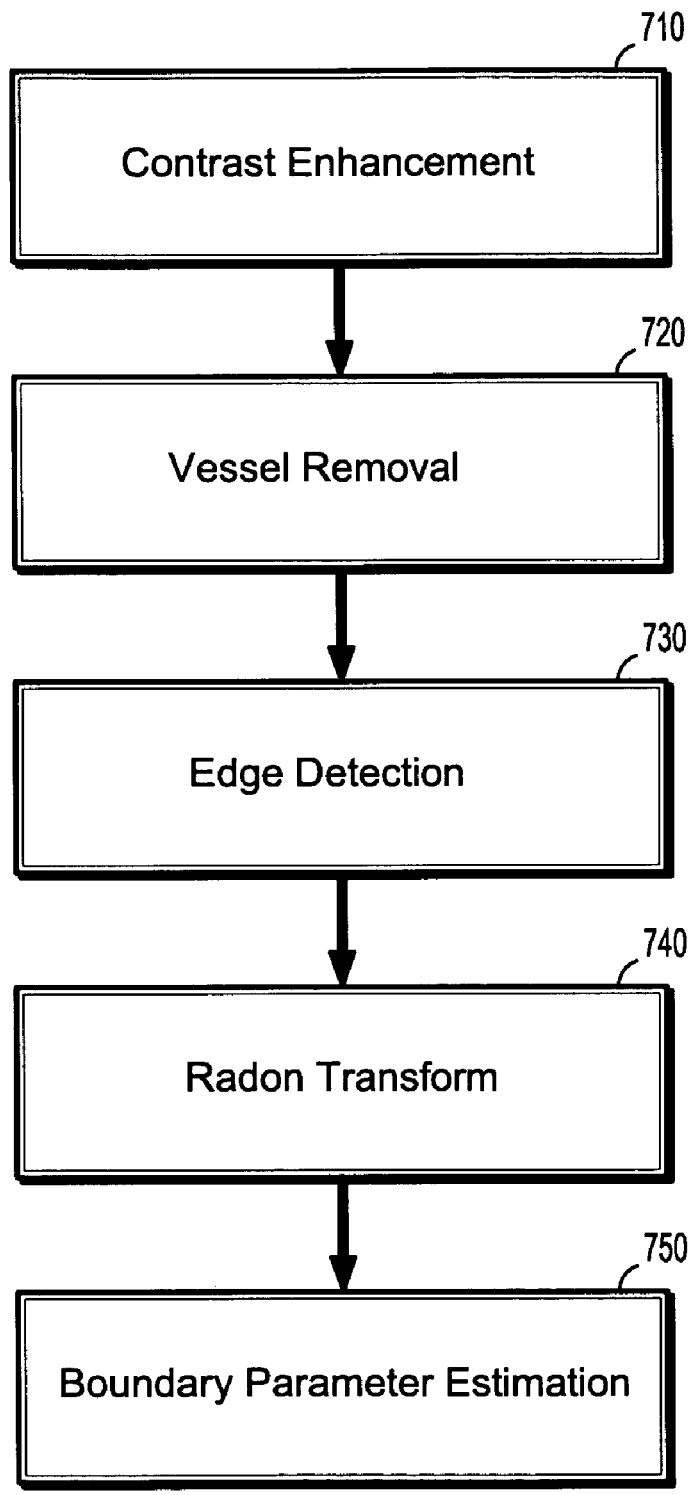
FIG. 7 illustrates a method for optic disk parameter estimation according to an exemplary embodiment of the present invention.
Figure 8:
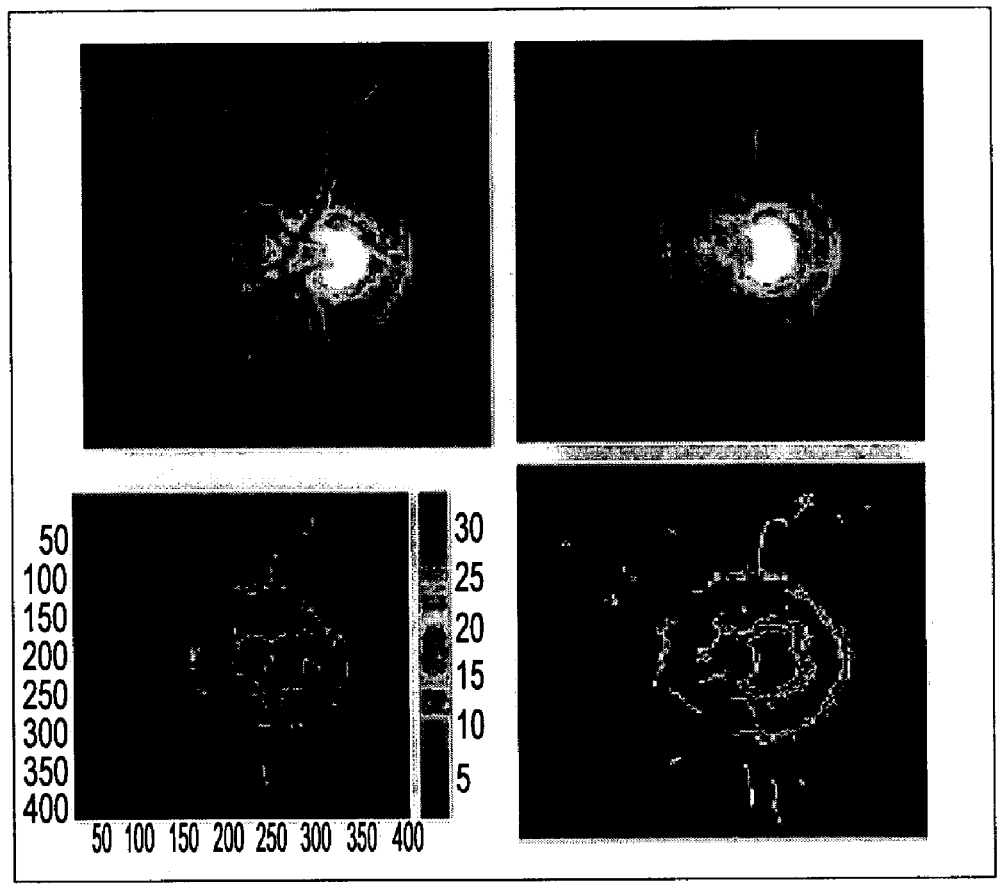
FIG. 8 illustrates effects of the method of FIG. 7 on a retinal image.

As shown in FIG. 7, the contrast of C1 is first enhanced using the approach described in K. Huang and M. Yan, "A local adaptive algorithm for microaneurysms detection in digital fundus images", Proceedings of Computer Vision for Biomedical Image Applications. Current Techniques and Future Trends, International Conference on Computer Vision Workshop, 2005 (710). An example of this is shown in the top-left image of FIG. 8. Vessels emerge from an optic disk and divide the region into multiple parts. To reduce the vessel effect on optic disk detection, morphological filtering is applied to remove vessel branches in a cropped image (720). Pixels on the vessel appear to be dark in gray value, thus a closing operation with a linear structure having a length of 25 pixels at four different orientations (e.g., 0, 45, 90 and 135 degrees) is applied to the image. A result of this is shown in the top-right image of FIG. 8. An edge detection filter is then applied to the image after vessel removal (730). A result of this is shown in the bottom-left image of FIG. 8. It is noted that a strong response is seen around the boundary of an optic disk and a weak response is seen in other regions. Thus, the edge map needs to be cleaned for further processing. Due to the variations existing in different images, using a fixed threshold for all edge maps is not viable. To remedy this, all edge maps are enhanced again as described in K. Huang and M. Yan, "A local adaptive algorithm for microaneurysms detection in digital fundus images", Proceedings of Computer Vision for Biomedical Image Applications: Current Techniques and Future Trends, International Conference on Computer Vision Workshop, 2005, to the maximum value of 255 in image intensity to reduce variations among different edge maps. A threshold of 250 in image intensity is applied to the enhanced map to obtain a binary map as shown in the bottom-right image of FIG. 8.

Figure 9:
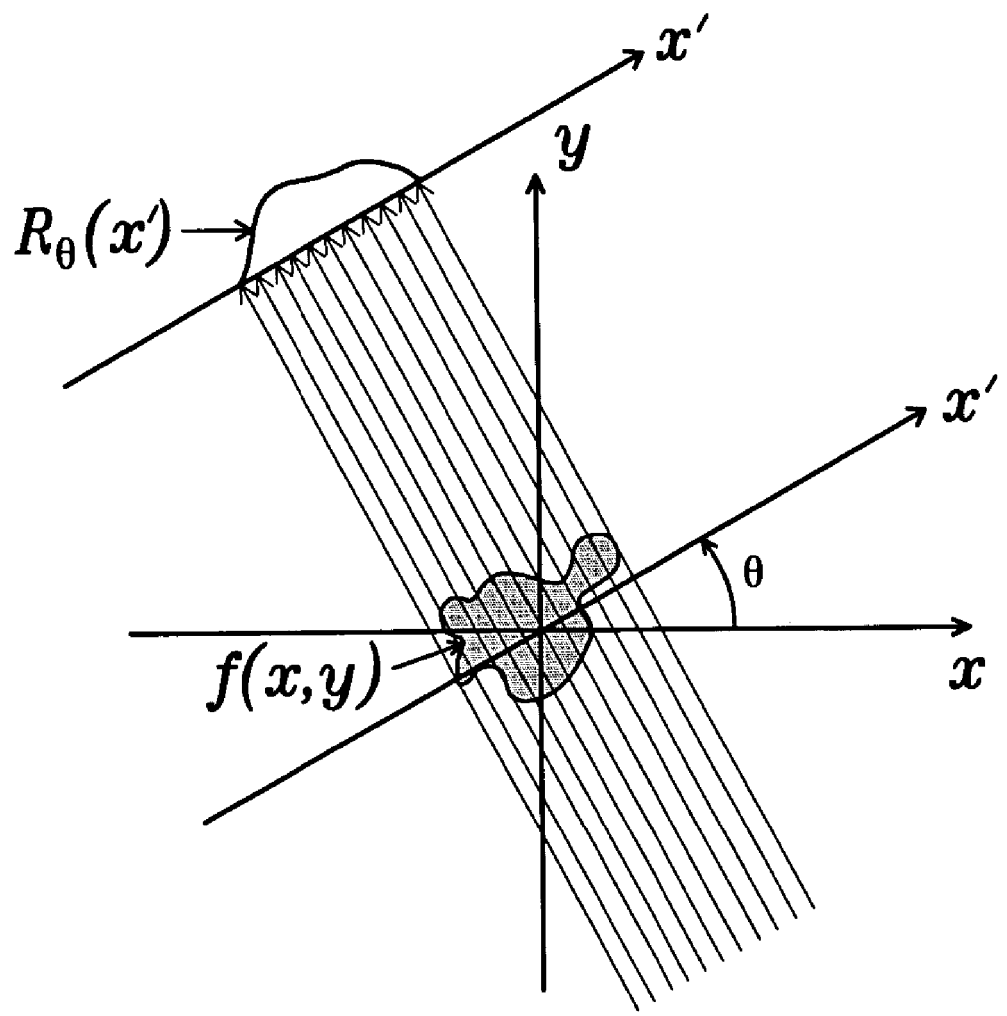
FIG. 9 illustrates a radon transform in the discrete domain.

In an ideal case, the detected edge map is a closed round structure. Thus, the horizontal and vertical projection of the structure would be used to unambiguously determine the radius and center of an optic disk. However, for the noisy edge map shown in FIG. 8, the simple method is not sufficient. To robustly and efficiently estimate the radius (R) and center (x,y) for a disk-like shape, a Radon transform is adopted. Rather than project an image in two orthogonal directions, Radon transform can project an image at any direction. Given a 2D continuous function $f(x,y)$, its Radon transform $R_\theta(x')$ at angle $\theta$ is as follows:

$$R_\theta(x')=\int f(x,y)\delta(x\cos\theta+y\sin\theta+x')dxdy \qquad (1)$$

where $\delta$ is the Dirac function. A Radon transform in the discrete domain is illustrated in FIG. 9.

Figure 10:
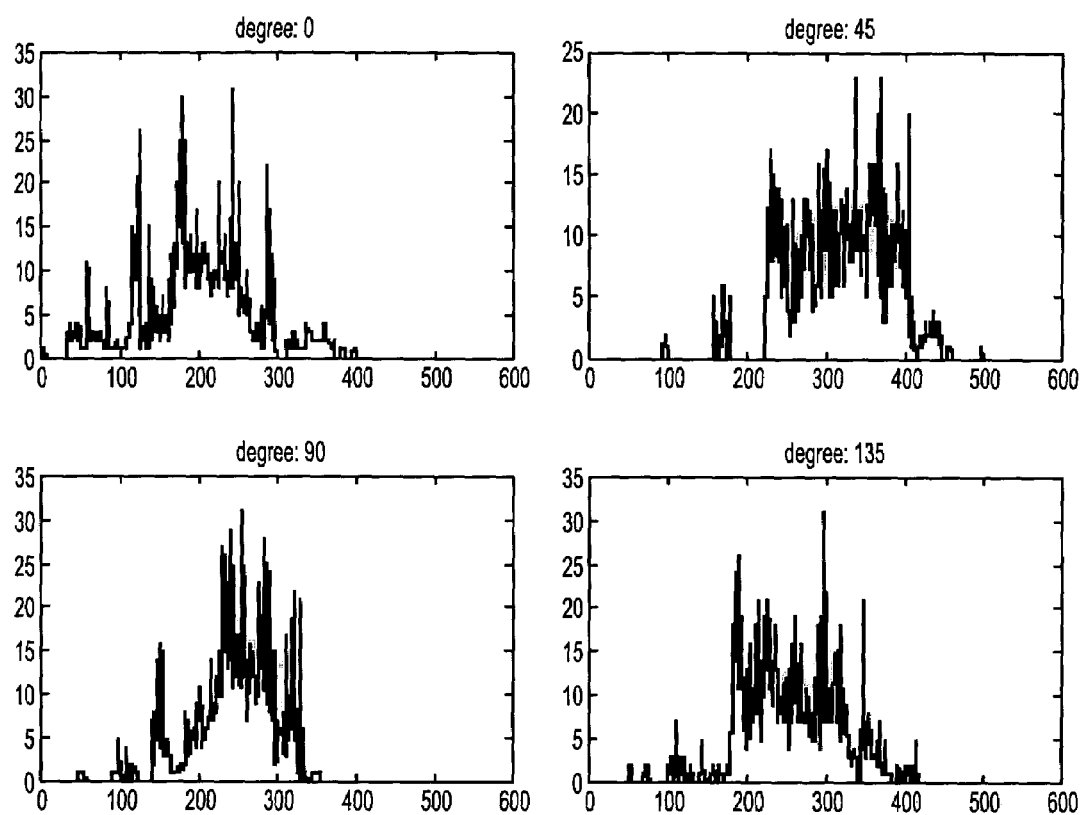
FIG. 10 illustrates radon transforms of an edge map at four angles before processing according to an exemplary embodiment of the present invention.

Using the Radon transform, the edge map is projected at different angles (740), and the radius and center of an optic disk are estimated jointly from these projections (750). However, the results of the Radon transform must be processed before parameter estimation. The processing includes two steps: identifying a major segment and trimming the major segment. As shown in FIG. 10, the projections are divided into multiple disconnected segments. Since Radon transforms of an edge map produce stronger responses at locations corresponding to the boundary of an optic disk, only a segment with the maximum number of pixels is kept and defined as the major segment. Values in other segments are set to zero. To further reduce the effect of noisy edges attached to the boundary of an optic disk, the major segment is trimmed from both the left and right sides. Denoting the major segments of the Radon transform as $H=\{h_1, h_2 \ldots h_N\}$, where N is the number of directions, the left and right trimming are conducted as follows.

1) $n = \max_{k,l}\{h_i\}/8$

2) $l = \operatorname{argmin}_{k,l}\{h_i > n\}$

3) $r = \operatorname{argmax}_{k,l}\{h_i > n\}$

4) $h_i = 0$, if $(i < l)$ or $(i > r)$

Denote the support of Radon transform $R_\theta(x')$ at angle $\theta$ as $[x_1', x_2']$, i.e., $R_\theta(x')=0$ for $x'<x_1'$ and $x'>x_2'$, the center $(X_c, Y_c)$ and radius R of an optic disk can be estimated from the following:

$$X_c\cos\theta + Y_c\sin\theta = \frac{1}{2}(x_1' + x_2') \quad (2)$$

$$R = \frac{1}{2}(x_2' - x_1') \quad (3)$$

Given Radon transforms of N different angles: $\{R_{\theta_1}(x'), R_{\theta_2}(x') \ldots R_{\theta_N}(x')\}$, there are $$\frac{1}{2}N(N-1)$$

estimated center positions $\{(X_1, Y_1), (X_1, Y_2) \ldots (X_M, Y_M)\}$ by solving equation (2), and N estimated radii $\{R_1, R_2, \ldots R_N\}$ from equation (3). It is often very difficult to obtain an edge map that captures the entire boundary of an optic disk, therefore projections at certain angles are not reliable. To address this, the mean and standard deviation are computed for the three sequences $\{X_i, 1\leq i\leq M\}$, $\{Y_i, 1\leq i\leq M\}$ and $\{R_i, 1\leq i\leq M\}$. The values from each sequence that are not within two standard deviations from its mean are removed. Furthermore, if a value in one sequence is removed, corresponding values in the other two sequences are also removed. Finally, the center and radius are estimated as the mean of remaining values from the three sequences.

Figure 11:
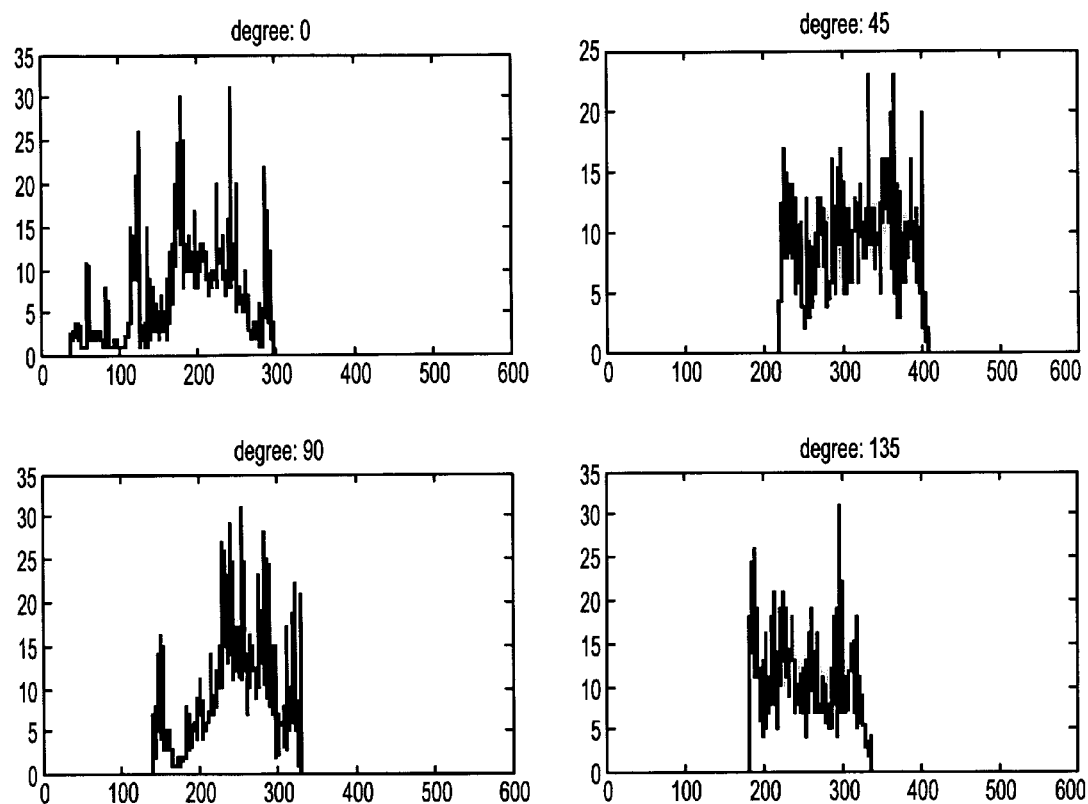
FIG. 11 illustrates radon transforms of an edge map at four angles after processing according to an exemplary embodiment of the present invention.
Figure 12:
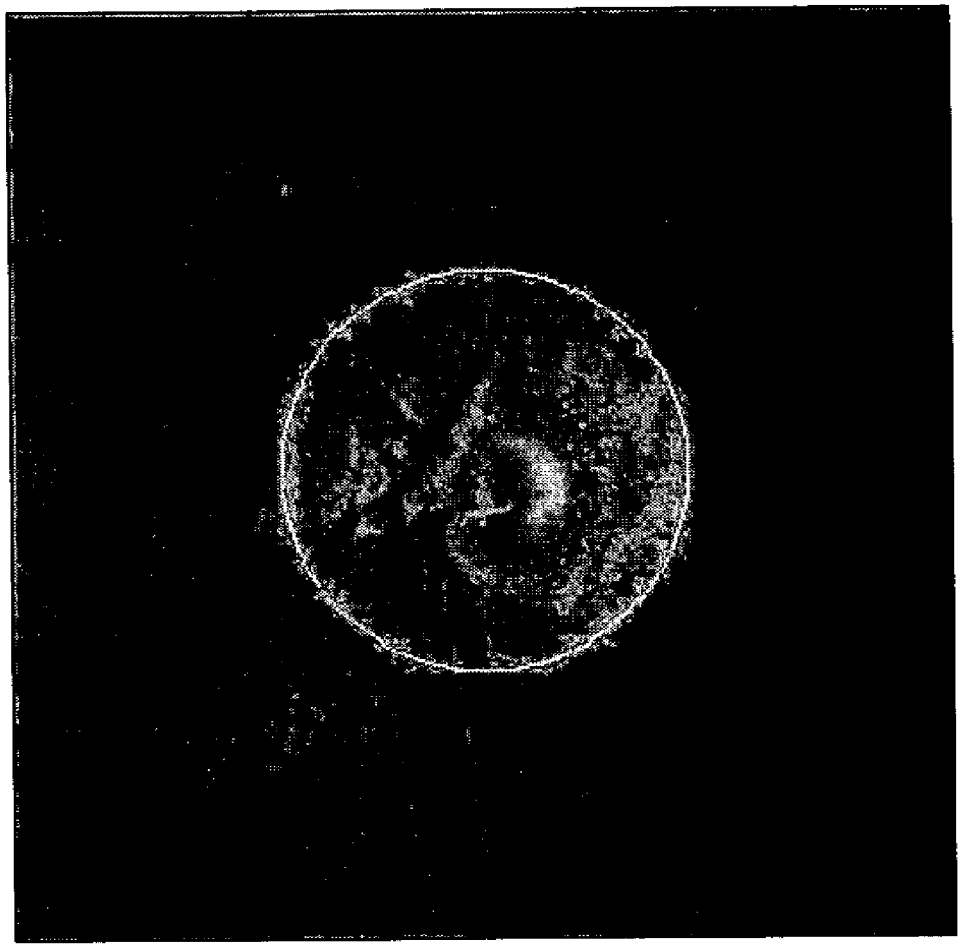
FIG. 12 illustrates a location and size of an optic disk estimated according to an exemplary embodiment of the present invention overlaid onto the image of FIG. 1.

As shown in FIG. 10, the radon transform is performed at four different angles: 0, 45, 90 and 135 degrees. The cleaned up version of the radon transforms of FIG. 10 is shown in FIG. 11. The estimated size of an optic disk is overlaid onto its corresponding image as shown in FIG. 12.

According to an exemplary embodiment of the present invention, a robust and computationally efficient scheme for estimating optic disk localization and boundary in retinal images is provided. In this scheme, an efficient two-level binarization algorithm is used to detect the major structure of vessels and a search algorithm is then applied to search the shortest path between the two points. An optic disk is localized as the intersection of the two searched shortest paths. The center and radius of an optic disk is directly estimated from a Radon transform of the edge map with vessel removal in a small area surrounding the estimated location. By combining Radon transforms taken from multiple angles, the parameter estimation is fairly robust to noise.

It should to be understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It is to be further understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for optic disk detection in retinal images, comprising:

extracting a vessel tree from a retinal image;

locating an optic disk in the retinal image using the vessel tree;

enhancing a contrast of the optic disk;

removing vessels from the contrast enhanced optic disk;

detecting a boundary of the optic disk with vessels removed by generating an edge map;

projecting the edge map at a plurality of angles by using a radon transform; and estimating a radius and center of the optic disk using the projections, wherein locating an optic disk in the retinal image comprises:

selecting first start and end points and second start and end points from different branches of the vessel tree;

finding a shortest path between the first start and end points and a shortest path between the second start and end points;
finding an intersecting point of the shortest paths at a root of the vessel tree; and
defining the intersecting point as a location of the optical disk.

2. The method of claim 1, wherein extracting a vessel tree from a retinal image comprises:
applying shade correction and contrast enhancement to the retinal image; and
performing a binarization on the shade corrected and contrast enhanced retinal image.

3. The method of claim 1, wherein selecting first start and end points and second start and end points from different branches of the vessel tree comprises;
defining a top-left point in the vessel tree as the first start point;
defining a bottom-right point in the vessel tree as the first end point;
defining a top-right point in the vessel tree as the second start point; and
defining a bottom-left point in the vessel tree as the second end point.

4. The method of claim 1, wherein the shortest paths are found by using a searching algorithm.

5. The method of claim 1, further comprising:
cropping the optic disk before enhancing a contrast of the optic disk.

6. The method of claim 5, wherein removing vessels from the contrast enhanced optic disk comprises:
applying a morphological filter to the cropped optic disk.

7. The method of claim 6, wherein generating the edge map comprises:
applying an edge detection filter to the cropped optic disk.

8. The method of claim 7, further comprising:
applying a threshold to the edge map to obtain a binary map.

9. The method of claim 1, further comprising:
before estimating a radius and center of the optic disk using the projections, identifying a portion of an edge map projected at one of the angles as the boundary of the optic disk; and
trimming left and right sides of the boundary of the optic disk.

10. A method for optic disk detection in retinal images, comprising:
extracting a vessel tree from a retinal image;
locating an optic disk in the retinal image using the vessel tree;
enhancing a contrast of the optic disk;
removing vessels from the contrast enhanced optic disk;
detecting a boundary of the optic disk with vessels removed by generating an edge map;
projecting the edge map at a plurality of angles by using a radon transform; and
estimating a radius and center of the optic disk using the projections,
wherein before estimating a radius and center of the optic disk using the projections, identifying a portion of an edge map projected at one of the angles as the boundary of the optic disk; and
trimming left and right sides of the boundary of the optic disk, and
wherein when estimating a radius and center of the optic disk using the projections,
computing a mean and standard deviation of each of three sequences, each sequence including an estimated value of a center or radius of the optic disk using the Radon transforms projected at each of the angles;
removing values from each of the sequences that are not with two standard deviations from each sequence's mean; and
estimating the radius and center of the optic disk by taking the mean of the remaining values of these sequences.

11. A system for optic disk detection in retinal images, comprising:
a memory device for storing a program;
a processor in communication with the memory device, the processor operative with the program to:
extract a vessel tree from a retinal image;
locate an optic disk in the retinal image using the vessel tree;
enhance a contrast of the optic disk;
remove vessels from the contrast enhanced optic disk;
detect a boundary of the optic disk with vessels removed by generating an edge map;
project the edge map at a plurality of angles by using a radon transform; and
estimate a radius and center of the optic disk using the projections,
wherein when locating an optic disk in the retinal image the processor is further operative with the program to:
select first start and end points and second start and end points from different branches of the vessel tree;
find a shortest path between the first start and end points and a shortest path between the second start and end points;
find an intersecting point of the shortest paths at a root of the vessel tree; and
define the intersecting point as a location of the optical disk.

12. The system of claim 11, wherein when extracting a vessel tree from a retinal image the processor is further operative with the program to:
apply shade correction and contrast enhancement to the retinal image; and
perform a binarization on the shade corrected and contrast enhanced retinal image.

13. The system of claim 11, wherein when selecting first start and end points and second start and end points from different branches of the vessel tree the processor is further operative with the program to:
define a top-left point in the vessel tree as the first start point;
define a bottom-right point in the vessel tree as the first end point;
define a top-right point in the vessel tree as the second start point; and
define a bottom-left point in the vessel tree as the second end point.

14. The system of claim 11, wherein the shortest paths are found by using a searching algorithm.

15. The system of claim 11, wherein the processor is further operative with the program to:
crop the optic disk before enhancing a contrast of the optic disk.

16. The system of claim 15, wherein when removing vessels from the contrast enhanced optic disk the processor is further operative with the program to:
apply a morphological filter to the cropped optic disk.

17. The system of claim 16, wherein when generating the edge map the processor is further operative with the program to:
apply an edge detection filter to the cropped optic disk.

18. The system of claim 17, wherein the processor is further operative with the program to:
apply a threshold to the edge map to obtain a binary map.

19. The system of claim 11, wherein before estimating a radius and center of the optic disk using the projections the processor is further operative with the program to:
identify a portion of an edge map projected at one of the angles as the boundary of the optic disk; and
trim left and right sides of the boundary of the optic disk.

20. A system for optic disk detection in retinal images, comprising:
a memory device for storing a program;
a processor in communication with the memory device, the processor operative with the program to:
extract a vessel tree from a retinal image;
locate an optic disk in the retinal image using the vessel tree;
enhance a contrast of the optic disk;
remove vessels from the contrast enhanced optic disk;
detect a boundary of the optic disk with vessels removed by generating an edge map;
project the edge map at a plurality of angles by using a radon transform; and
estimate a radius and center of the optic disk using the projections,
wherein before estimating a radius and center of the optic disk using the projections the processor is further operative with the program to:
identify a portion of an edge map projected at one of the angles as the boundary of the optic disk; and
trim left and right sides of the boundary of the optic disk, and
wherein when estimating a radius and center of the optic disk using the projections, the processor is further operative with the program to:
compute a mean and standard deviation of each of three sequences, each sequence including an estimated value of a center or radius of the optic disk using the Radon transforms projected at each of the angles;
remove values from each of the sequences that are not with two standard deviations from each sequences mean; and
estimate the radius and center of the optic disk by taking the mean of the remaining values of these sequences.

* * * * *